Figure 1:
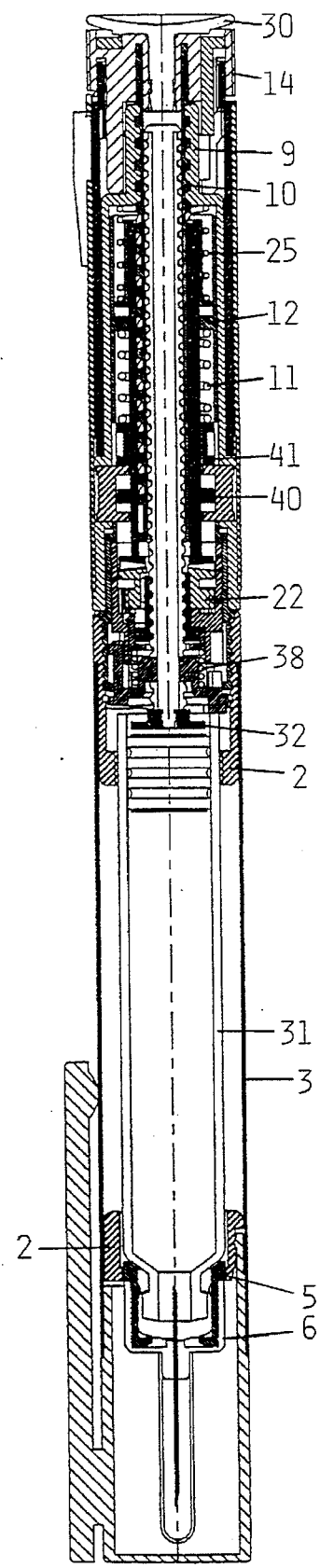

United States Patent

Petersen et al.

[11] Patent Number: 5,626,566
[45] Date of Patent: May 6, 1997

[54] LARGE DOSE PEN

[75] Inventors: Lars P. K. Petersen, Gentofte; Niels-Aage B. Hansen, Havdrup, both of Denmark

[73] Assignee: Novo Nordisk A/S, Bagsvaerd, Denmark

[21] Appl. No.: 211,131

[22] PCT Filed: Sep. 7, 1992

[86] PCT No.: PCT/DK92/00267
§ 371 Date: Mar. 24, 1994
§ 102(e) Date: Mar. 24, 1994

[87] PCT Pub. No.: WO93/07922
PCT Pub. Date: Apr. 29, 1993

[30] Foreign Application Priority Data

Oct. 18, 1991 [DK] Denmark ................. 1754/91

[51] Int. Cl.⁶ ................................................. A61M 5/00
[52] U.S. Cl. ................ 604/208; 604/211; 222/47; 222/309; 222/390
[58] Field of Search ........................ 604/207–209, 604/232, 234, 135, 210, 211, 218, 131–134, 136, 139, 187, 181; 222/46–48, 16, 18, 282, 283, 309, 310, 325, 326, 336, 386, 390

[56] References Cited

U.S. PATENT DOCUMENTS

| | | | |
|---|---|---|---|
| 4,592,745 | 6/1986 | Rex et al. | 604/211 |
| 4,810,249 | 3/1989 | Haber et al. | 604/210 |
| 4,865,591 | 9/1989 | Sams | 604/208 |
| 4,936,833 | 6/1990 | Sams | 604/209 |
| 4,973,318 | 11/1990 | Holm et al. | |
| 5,017,190 | 5/1991 | Simon et al. | 604/208 |
| 5,092,842 | 3/1992 | Bechtold et al. | 604/135 |
| 5,104,380 | 4/1992 | Holman et al. | 604/211 |
| 5,114,406 | 5/1992 | Gabriel et al. | 604/134 |
| 5,226,895 | 7/1993 | Harris | 604/211 |
| 5,244,465 | 9/1993 | Michel | 604/208 |

FOREIGN PATENT DOCUMENTS

| | | |
|---|---|---|
| 0293572 | 12/1988 | European Pat. Off. . |
| 0327910 | 8/1989 | European Pat. Off. . |
| 0450905 | 10/1991 | European Pat. Off. . |
| 0496141 | 7/1992 | European Pat. Off. . |

*Primary Examiner*—Vincent Millin
*Assistant Examiner*—Ronald K. Stright, Jr.
*Attorney, Agent, or Firm*—Steve T. Zelson, Esq.; James Harrington, Esq.

[57] ABSTRACT

A pen shaped syringe for repetitive injection of individually set doses of a medicine from a cylinder ampoule reservoir comprises a dose setting member which may be rotated to cause a rotative movement of a dosing member and a combined rotative and axial movement of an indicator member indicating the set dose, and a piston drive member which when rotated in one direction moves the piston into the cylinder ampoule. A unidirectional coupling is established between the dosing member and the piston drive member by each member carrying a disc having surfaces with sector shaped saw teeth riding over each other when the dosing member is rotated in the dose setting direction and engaging each other when the dosing member is rotated in the opposite direction corresponding to the direction of rotation by which the piston is moved into the cylinder ampoule. A nut/screw connection is established between a syringe housing and the dose setting member, and means are provided to release the unidirectional coupling between the piston drive member and the dosing member by drawing the coupling discs away from each other.

6 Claims, 2 Drawing Sheets

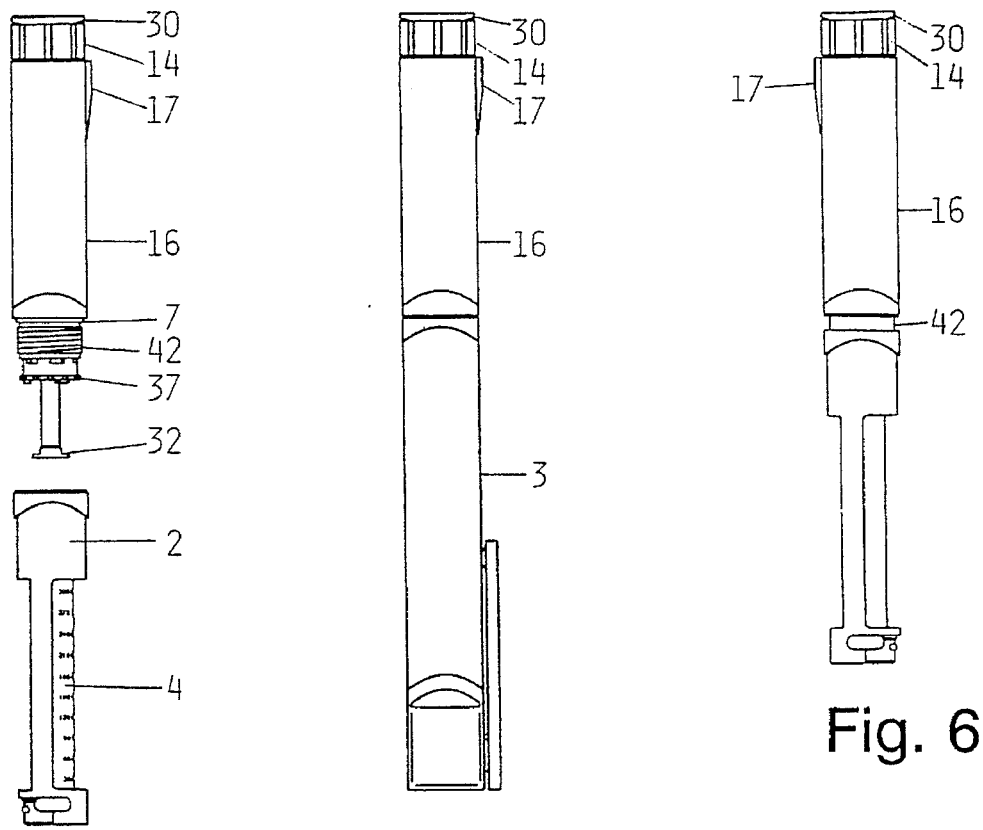
Fig. 6
Fig. 5
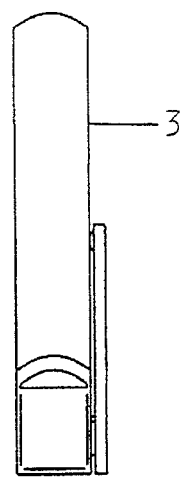
Fig. 4
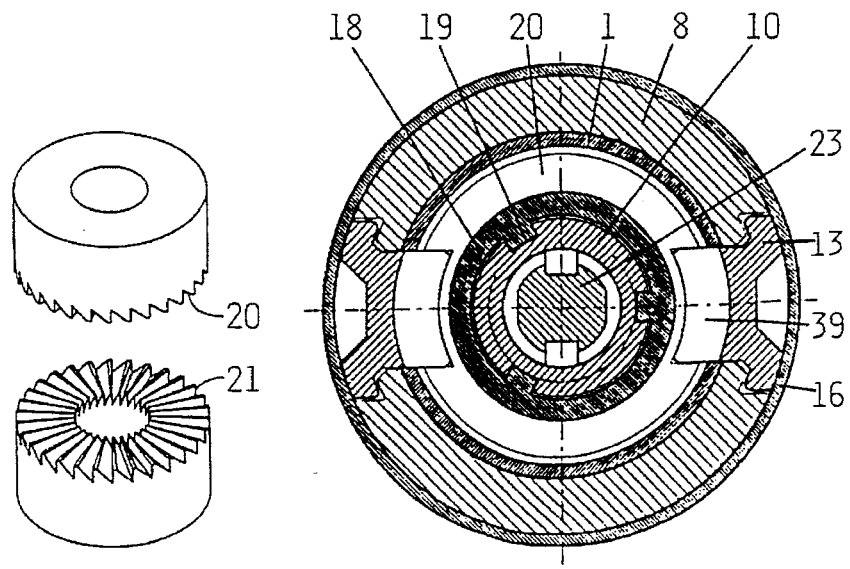
Fig. 7
Fig. 3

LARGE DOSE PEN

CROSS REFERENCE TO RELATED APPLICATIONS

This application is a 35 USC 371 of PCT/DK92/00267 filed Sep. 7, 1992, the contents of which are incorporated herein by reference.

The invention relates to a pen shaped syringe for repetitive injection of individually set doses of a medicine from a reservoir in the syringe.

Such pen syringes are especially used by diabetics who have to inject themselves frequently with an insulin preparation to keep their blood glucose level within tolerable limits.

With the appearance of insulin preparations having a retarded action and of mixed preparations which make it possible to inject at the same time a preparation meeting an immediate need for insulin and a preparation covering the basic need for a long time, the time between injections is increased and so are the doses administered at each injection.

The doses are mainly set by rotating part of the pen syringe relatively to the rest of the syringe and numbers forming a scale along an edge of the one rotatable part of the syringe are moved in relation to an indicating mark on the rest of the syringe to indicate the set dose. Hereby the dose is limited by the fact that only a limited number of numbers can be placed along the edge of the rotatable part if they shall be readable at all. This problem is overcome by imparting the rotatable part an axial displacement concurrently with its rotation whereby instead of a circle a helical line becomes available for dose indicating numbers and even a scale covering rotation in excess of one turn.

The pen syringe should be as simple as possible to use, i.e. the normal use should only imply setting a dose and injecting the set dose, and both these steps should be simple to perform and this condition is met by most pen syringes. However, not all pen syringes offer the opportunity to cancel a set dose, so if a dose once set is not wanted for injection the only way to bring the syringe back in its neutral position is to spill the dose. With syringes by which large doses may be set this is not acceptable.

By a known type of syringe the scale is arranged along a helix having just one turn. A helical recess in a cylinder surface of a dose setting member is engaged by a pin on the syringe housing so that the dose setting member when rotated is axially displaced along its axis. After having been axially displaced by the setting of a dose, the dose setting member is pressed home to inject the dose. The engagement between the pin and the helical recess will cause a rotation of the dose setting member when it is axially pressed home, this rotation being in the opposite direction of the rotation for setting the dose. The rotation of the dose setting member is transferred to a screw/nut mechanism driving a piston in the syringe forward a distance proportional to the rotation.

The ends of the one turn helical recess are connected by an axial recess. This enables the setting member to be pressed axially back without imparting a rotary movement to this member if the rotary position of the member is so that the pin on the syringe housing engages the axial recess instead of the helical part of the recess. In this way a set dose may be cancelled by turning the dose setting member further until the pin engages the axial recess. However, this cancelling feature limits the effective dose setting rotation of the dose setting member to a little less than one turn, and further, as the demands for precision of the injected dose set a limit to the size of the dose per turning of the screw/nut mechanism, the size of the possible set dose is heavily restricted.

Consequently, it is the object of the invention to provide a pen syringe by which large doses may be set, a set dose may be cancelled, and the possibility of cancellation does not influence the possible size of a set dose or the simplicity of the normal use of the syringe.

This is obtained by a pen shaped syringe for repetitive injection of individually set doses of a medicine from a cylinder ampoule reservoir, comprising a dose setting member which may be rotated to cause a rotative movement of a dosing member and a combined rotative and axial movement of an indicator member indicating the set dose, a piston drive member which when rotated in one direction moves the piston into the cylinder ampoule, a unidirectional coupling between the dosing member and the piston drive member, the coupling being so directed that a dose setting rotation of the dosing member is not transferred to the piston drive whereas a rotation in the opposite direction is, this syringe being characterized in, that a nut/screw connection is established between a syringe housing and the dose setting member, and that means are provided to release the unidirectional coupling between the piston drive member and the dosing member.

The nut/screw connection provides by mutual engaging threads a more stable guidance of the dose setting member than does a pin engaging a recess. As the cancelling mechanism is not based on an axial recess as a return path, the dosing rotation of the dose setting member may be performed for more than one turn, and thereby it is permitted to set a larger dose than the one which can be provided by rotating the piston drive one turn. The cancelling mechanism is realized as a coupling which may disconnect the dosing member from the piston drive, so that the dose setting member and the dosing member may be rotated back without the rotation being transmitted to the piston drive.

The thread of the screw/nut connection of the dosing member and the housing may have a pitch angle exceeding the friction angle of the nut and screw. Thereby the dosing rotation of the dose setting member may be obtained by simply pressing this member axially back, whereby the screw will automatically screw itself through the nut and provide a rotative movement of the dose setting member in the dosing direction. This automatic dosing screw function may more easily be obtained if the outer end of the dosing member is terminated by a knob wherein a press button is journaled, the button and the knob having mutually abutting surfaces made of materials having a friction angle lower than the friction angle of the nut/screw connection.

According to an embodiment of the invention, the dose setting member may comprise a threaded spindle, the dosing member may be tubular and fit over this spindle, and the spindle may have axial recesses engaged by corresponding axial beams on the inner side of the bore of the dosing member. Thereby a dosing member is provided which will follow rotary but not axial movements of the dose setting member.

The unidirectional coupling between the dosing member and the piston drive may be provided by coupling parts having circular surfaces provided with sector shaped teeth having an abrupt and a ramp shaped edge, the surfaces by a spring being forced against each other with the ramp shaped edge of the teeth on so one surface abutting the ramp shaped edge of the teeth on the other surface. When the dose setting member is rotated in the dose setting direction, the teeth on the coupling parts will slide with their ramp shaped parts over each other, whereby the dosing member is axially displaced against the force of the spring and will jump back each time an abrupt edge of the teeth is reached. Each jump back may be heard and sensed by the operator, and the pitch of the toothing may be chosen so that a jump back takes place each time the dose setting is increased by say one unit.

The coupling mechanism may be provided by the syringe having a tubular basic element, a tubular element surrounding the basic element coaxially with it and axially displaceable in relation thereto against the force of a spring forcing the tubular element to a fixed position on the basic element, and a lifting fork carried by the tubular element and engaging an outer annual projection on the dosing member to lift the coupling part thereof out of engagement with the coupling part of the piston drive when the tubular member is axially displaced on the basic element against the force of the spring away from its fixed position.

Figure 2:
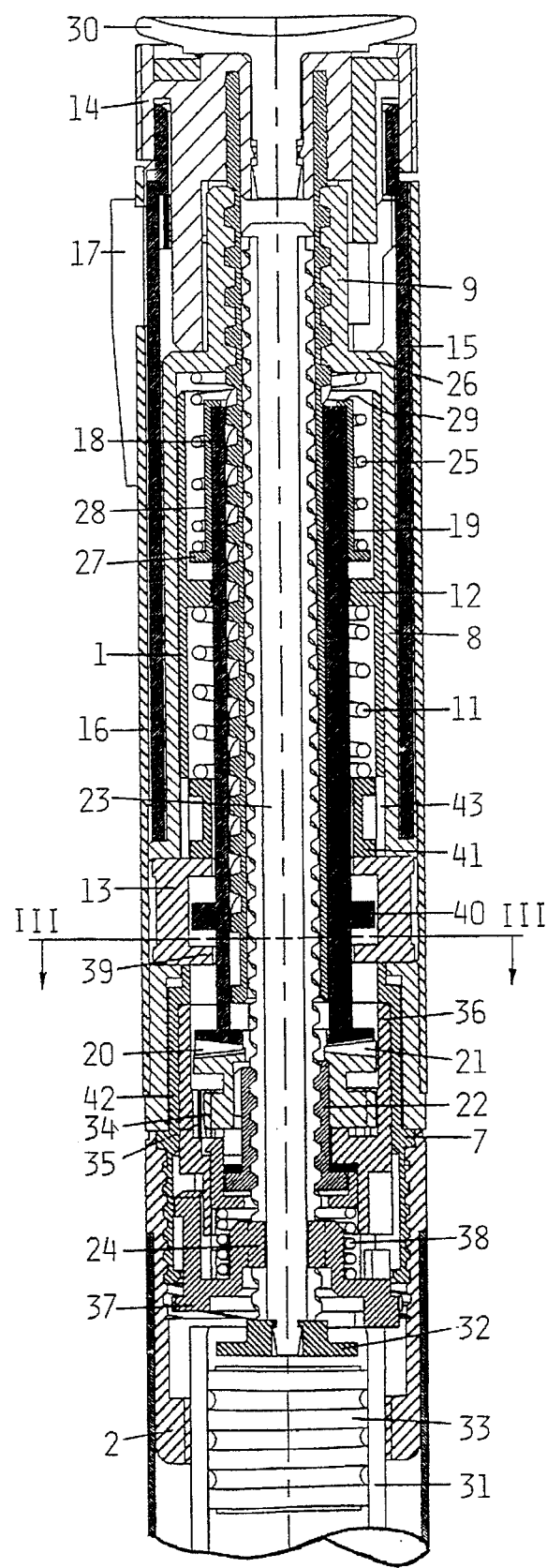

In the following the invention will be further described with references to the drawings, wherein FIG. 1 is a sectional side view of a pen shaped syringe according to the invention, FIG. 2 is an enlarged view of the part of the syringe in FIG. 1 containing the dosing mechanism, FIG. 3 shows a cross section along the line III—III in FIG. 2, FIG. 4 shows a side view of the pen syringe in FIG. 1 separated into a part comprising the dosing mechanism, a cartridge holder, and a cap, FIG. 5 shows the syringe in FIG. 4 put together, FIG. 6 shows a side view of the syringe with the cap removed and the dosing mechanism part and the cartridge holder drawn away from each other to allow a cancelling of a set dose, and FIG. 7 shows schematically the coupling discs of a unidirectional coupling.

The pen syringe shown in FIGS. 1–6 is built up around a tubular basic member 1 having at its one end a part 42 with enlarged diameter, this part by an annular projection being divided into two, a first part being provided with a thread onto which a cartridge holder 2 may be screwed and a second part receiving a tubular member 8. The cartridge holder 2 comprises a tubular element designed to accommodate a cartridge and having in its side walls axially extending openings through which the contents of the cartridge may be inspected. Along one of the openings a recessed part 4 of the side wall is provided with a scale showing the available amount of medicine, here as the number of international units of insulin. At its distal end the cartridge holder 2 is provided with not seen protrusions protruding inwardly from the cartridge holder wall to hold back the cartridge in the holder and cooperating with an adapter top 5 on the neck part of the cartridge. This adaptor top 5 protrudes from the end of the cartridge holder 2 and is provided with an outer thread onto which a needle hub 6 is screwed to secure the cartridge in the holder 2. A tubular protective cap 3 may be passed over the cartridge holder 2 when the syringe is not in use.

The tubular member 8 fits with its one end over the second part of the enlarged diameter part 42 of the one end of the basic member 1 and abuts with its edge against the annular projection 7. The other end of the tubular member 8 has a reduced diameter and fits over the basic member 1 and is at its outer end surmounted by a part 9 having a further reduced diameter and carrying an internal thread in engagement with an outer thread on a tubular spindle 10.

A spring 11 abutting at its one end an annular internal projection 12 in the bore of the basic member 1 and pressing at its other end against a bushing 41 transferring the pressure to a set of lifting forks 13, the function of which will be described below, and which forks 13 carried guidingly in openings spaced along the perimeter of the member 8 transfer the pressure to the member 8 keeping the edge thereof in abutment with the projection 7 on the basic member 1. Through slots 43 in the wall of the tubular basic member 1 the lifting forks 13 project into the bore of the basic member and may be displaced axially in these slots.

The spindle 10 is at its end extending beyond the part 9 secured to a dose setting knob 14 and may be rotated by rotating this knob 14. When rotated in one direction the spindle 10 and consequently the knob 14 are displaced axially away from the tubular member 8.

An indicating sleeve 15 is secured to the knob 14 and forms a skirt dependent from the knob 14 and being accommodated in the space between the member 8 and a tubular housing 16 mounted on the large diameter part of this member 8. A window in the tubular housing 16 is provided with a magnifying glass 17, through which the sleeve 15 may be inspected along a helical line, when it is rotated and simultaneously axially displaced along with the knob 14. Numbers indicating a set dose are printed along the helical line to show the actual dose through the magnifying glass 17.

Rotation of the spindle 10 is transferred to a tubular dosing member 18 fitting over the thread of the spindle 10. The transmission is accomplished by the spindle 10 having one or more axial recesses in its thread engaged by axial beams 19 on the inner surface of the dosing member 18. Thereby rotative motion is transferred whereas axial motion is not.

At its end opposite the knob 14 the dosing member 18 forms a part 20 of a unidirectional coupling through which the member 18 is coupled to a piston drive comprising a coupling part 21 and a drive nut 22 having an internal thread engaging an external thread on a piston rod 23 which is in its retracted position accommodated in the bore of the tubular spindle 10 and which is made unrotatable relatively to the basic member 1 by locking projections 24, which are mounted unrotatably in relation to the basic member 1 and engage axial slots in the thread of the piston rod 23.

The unidirectional coupling is provided by the dosing member 18 and the piston drive nut 22 having disc shaped coupling parts 20 and 21, respectively, having at the surfaces facing each other teeth each forming a part of a sector and each having a ramp shaped and an abrupt edge. These discs are shown schematically in FIG. 7. The toothed surfaces are urged against each other by a spring 25 compressed between a shoulder 26 at the upper end of the tubular member 8 and an outward flange 27 at one end of a bushing 28 having at its other end an inward flange 29 abutting the upper edge of the dosing member. When the dosing member is rotated in the direction by which the knob is screwed outwardly, the ramp shaped edges slide along each other displacing the coupling members away from each other against the force of the spring 25 until the abrupt edge is reached and the coupling part is displaced home by the force of the spring ready to start a new sliding along the ramp shaped parts. This overriding prevents the rotation from being transmitted to the piston drive nut 22 when the knob is rotated in the dose setting direction but is transmitted when the knob is rotated in the opposite direction, as the abrupt edges on the coupling parts will then engage each other. This rotation may be provided by pressing the knob home axially, the thread of the spindle having a pitch allowing it to transform the axial pressure to a rotation. To ease this mechanism the knob 14 is provided with a press button 30 journaled in the knob 14 with a lower surface of the button abutting an upper surface of the knob, the abutting surfaces being made of materials which ensure low friction.

The rotation is transmitted to the piston drive part 21 of the coupling and consequently to the piston drive nut 22. When the nut 22 is rotated by the transmitted rotation it will drive the unrotatable piston rod 23 in an axial direction towards the cylinder ampoule 31, and by a piston foot 32 the piston rod will press a piston 33 into the cylinder ampoule 31.

The piston drive part 21 of the coupling is at its periphery provided with resilient teeth 34 which collaborate with internal teeth 35 in a tubular member 36 rigidly mounted in the basic member 1 to provide a detent allowing rotation of the piston drive nut 22 in an injecting direction but preventing rotation of the nut 22 in the opposite direction.

The piston rod 23 is made unrotatable by having an axial recess engaged by locking projections 24 on a piston rod lock member 37. Against the force of a spring 38 this member is by the upper edge of the cylinder ampoule 31 pressed into the end of the basic member 1 in an unrotatable engagement. When cartridge holder 2 containing the cylinder ampoule 31 is dismounted by unscrewing it from the basic member 1, the spring 38 will press the piston rod lock member 37 free of the basic member 1, and the piston rod may now be rotated as the lock member 37 may now rotate with it. Thereby the piston rod may be screwed back through the piston drive nut 22 to its retracted position. When the cartridge holder with a new ampoule is screwed onto the basic member 1, the lock member 37 is pressed back into its unrotatable engagement with the basic member and the piston rod is again made unrotatable.

From the functions described it is seen that a dose may be set by rotating the knob 14 in the direction causing a disengaging relative movement of the coupling parts 20 and 21. The parts 20 and 21 are appropriately toothed in a way making each of the hearable sudden displacements at the end of the ramps of a pair of teeth sliding along each other correspond to e.g. one unit. When the knob 14 is screwed home, which may be done by pressing the button 30, the rotation is transmitted to the piston drive nut 22 causing a forward movement of the piston corresponding to the set dose.

If a set dose should be cancelled it is obtained by gripping the cartridge holder 2, which is secured to the basic element 1, and the tubular housing 16, which is secured to the tubular member 8, and by drawing the cartridge holder 2 and the tubular housing 16 axially away from each other. Thereby the tubular member 8 is axially displaced in relation to the basic member 1, and the spring 11 maintaining the tubular member 8 in position on the basic member 1 is further compressed. By this displacement the lifting forks 13 inserted in openings in the tubular member 8 are displaced until the lower one of their prongs 39 extending inwardly through slots in the basic member 1 abuts an annular projection 40 on the dosing member 18. A further displacement against the force of the spring 11 will displace the dosing member 18 against the force of the spring 25 and bring the coupling parts 20 and 21 out of their mutual engagement. Now the dosing part can freely be rotated without the rotation being transmitted to the piston drive nut, and consequently a set dose may be cancelled by turning the dose setting knob 14 back to its initial position, possibly by pressing it home.

When released the member 8 will by the spring 11 be pressed back into its original position, and the dosing member 18 will be moved back by the spring 25 to its nut driving position.

We claim:

1. An apparatus for use with a pen shaped syringe for repetitive injection of individually set doses of a medicine from a cylinder ampoule reservoir, comprising:

a housing, a nut member with an internal thread fixed in the housing, a dose setting member rotatable in a fist direction to set a dose and in a second direction to inject a set dose, and comprising a spindle with an external thread engaging the internal thread of said nut member, a dosing member coupled to the dose setting member to be rotated with this dose setting member, an indicator member, rigidly connected to the dose setting member to follow axial and rotational movement of this dose setting member, a piston drive member which when rotated in said second direction moves a piston into the cylinder ampoule, a unidirectional coupling provided between the dosing member and the piston drive member, by a first coupling part on the dosing member engaging a second coupling part on the piston drive member and so directed that the rotation of dosing member induced by dose setting rotation of the dose setting member is not transmitted to the piston drive member whereas rotation in the opposite dosing direction is; wherein a nut/screw connection is established between the housing and the dose setting member and means are provided to optionally release the unidirectional coupling between the dosing member and the piston drive member.

2. An apparatus according to claim 1, wherein the dose setting member is tubular with a bore fitting over the spindle of the dose setting member, which spindle has axial recesses engaged by corresponding axial beams on the inner side of the bore of the dosing member.

3. An apparatus according to claim 2, wherein the unidirectional coupling between the dosing member and the piston drive member is provided by said first and second coupling parts having circular surfaces provided with sector shaped teeth having an abrupt and a ramp shaped edge, the surfaces being forced against each other by a first spring with the ramp shaped edges of the teeth on one surface abutting the ramp shaped edges of the teeth on the other surface; said first spring surrounding a part of the dosing member and having a first and a second end, the first end abutting a shoulder in the housing and the second end abutting an outward flange on a first bushing which is fitted on an end of the dose member and further has an inward flange resting on said end of the dose member.

4. An apparatus according to claim 3, wherein the means to optionally release the coupling between the dosing member and the piston drive member comprises a tubular basic element having a first end with an enlarged diameter carrying a cartridge holder accommodating an ampoule, and a second end coaxially surrounded by a tubular element having a first end with an enlarged diameter fitting into an end of the housing and fixed to said housing, and a second end with a reduced diameter forming the nut member, the tubular element being axially displaceable from a fixed position relative to the basic element against the force of a second spring inside said basic element and having a first end abutting an internal projection in said basic element and a second end abutting a second bushing resting on lifting forks which are carried in the wall of the tubular element in openings perpendicular to the axis; an outer projection on the dosing member projects into a space between the arms of the forks so that the forks lift the first coupling part, on the dosing member, out of engagement with the second coupling part of the piston drive, when the tubular member is displaced on the basic element.

5. An apparatus according to claim 1, wherein the internal thread of the nut member and the external thread of the spindle of the dose setting member have a pitch allowing transformation of an axial pressure to a rotation.

6. An apparatus syringe according to claim 5, wherein an outer end of the dose setting member is terminated by a knob wherein a press button is journaled, the button and the knob having mutually abutting surfaces made of materials ensuring low friction.

* * * * *